(12) United States Patent
Spencer et al.

(10) Patent No.: US 7,765,670 B2
(45) Date of Patent: Aug. 3, 2010

(54) METHOD TO SIMULTANEOUSLY LOAD AND COVER SELF EXPANDING STENTS

(75) Inventors: Steve M. Spencer, Minneapolis, MN (US); Karl A. Jagger, Deephaven, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1096 days.

(21) Appl. No.: 10/917,780

(22) Filed: Aug. 13, 2004

(65) Prior Publication Data

US 2006/0036310 A1 Feb. 16, 2006

(51) Int. Cl.
*B23P 11/02* (2006.01)
(52) U.S. Cl. .......................... 29/451; 29/516
(58) Field of Classification Search ................ 623/1.11, 623/1.13, 1.12; 29/516, 448, 451
See application file for complete search history.

(56) References Cited

U.S. PATENT DOCUMENTS

| | | | | |
|---|---|---|---|---|
| 3,490,136 | A * | 1/1970 | Stickley | 29/426.2 |
| 3,509,617 | A * | 5/1970 | Winter | 228/115 |
| 4,489,473 | A * | 12/1984 | Nakagami | 29/451 |
| 5,091,205 | A | 2/1992 | Fan | 427/2.28 |
| 5,261,263 | A * | 11/1993 | Whitesell | 72/409.19 |
| 5,443,458 | A * | 8/1995 | Eury | 604/891.1 |
| 5,637,113 | A * | 6/1997 | Tartaglia et al. | 623/1.42 |
| 5,690,644 | A | 11/1997 | Yurek et al. | 623/1.11 |
| 5,700,286 | A * | 12/1997 | Tartaglia et al. | 623/1.15 |
| 5,718,973 | A * | 2/1998 | Lewis et al. | 623/1.32 |
| 5,725,519 | A * | 3/1998 | Penner et al. | 606/1 |
| 5,755,770 | A | 5/1998 | Ravenscroft | 623/1.13 |
| 5,772,669 | A | 6/1998 | Vrba | 623/1.11 |
| 5,824,046 | A * | 10/1998 | Smith et al. | 623/1.13 |
| 5,836,952 | A * | 11/1998 | Davis et al. | 606/108 |
| 5,906,759 | A * | 5/1999 | Richter | 219/121.63 |
| 5,920,975 | A * | 7/1999 | Morales | 29/282 |
| 5,928,279 | A * | 7/1999 | Shannon et al. | 623/1.13 |
| 5,948,191 | A | 9/1999 | Solovay | 156/86 |
| 5,968,069 | A | 10/1999 | Dusbabek et al. | 606/194 |
| 5,992,000 | A * | 11/1999 | Humphrey et al. | 29/516 |
| 6,004,328 | A | 12/1999 | Solar | 623/1.11 |
| 6,009,614 | A * | 1/2000 | Morales | 29/516 |
| 6,063,092 | A | 5/2000 | Shin | 606/108 |
| 6,068,634 | A | 5/2000 | Lorentzen et al. | 623/1.11 |
| 6,082,990 | A * | 7/2000 | Jackson et al. | 425/517 |
| 6,096,027 | A * | 8/2000 | Layne | 606/1 |
| 6,120,522 | A | 9/2000 | Vrba et al. | 606/190 |
| 6,141,855 | A * | 11/2000 | Morales | 29/516 |
| 6,290,722 | B1 * | 9/2001 | Wang | 623/1.46 |

(Continued)

FOREIGN PATENT DOCUMENTS

EP 0716836 A1 6/1996

*Primary Examiner*—Todd E Manahan
*Assistant Examiner*—Erin Colello
(74) *Attorney, Agent, or Firm*—Vidas, Arrett & Steinkraus, P.A.

(57) ABSTRACT

A medical device may be secured to a medical device delivery apparatus by providing a wrapped medical device, the wrapped medical device comprising a medical device with a polymeric sheet disposed thereabout, compressing the wrapped medical device and affixing at least one opposing edge of the polymeric sheet to a portion of the polymeric sheet adjacent thereto so as to form a sheathed medical device and securing the sheathed medical device to a medical device delivery apparatus.

24 Claims, 9 Drawing Sheets

U.S. PATENT DOCUMENTS

| | | | |
|---|---|---|---|
| 6,302,893 B1 | 10/2001 | Limon et al. | 606/108 |
| 6,309,383 B1 * | 10/2001 | Campbell et al. | 606/1 |
| 6,360,577 B2 * | 3/2002 | Austin | 72/402 |
| 6,387,117 B1 * | 5/2002 | Arnold et al. | 623/1.1 |
| 6,416,536 B1 | 7/2002 | Yee | 623/1.11 |
| 6,432,130 B1 * | 8/2002 | Hanson | 623/1.11 |
| 6,443,979 B1 | 9/2002 | Stalker et al. | 623/1.11 |
| 6,510,722 B1 * | 1/2003 | Ching et al. | 72/402 |
| 6,533,806 B1 | 3/2003 | Sullivan et al. | 623/1.11 |
| 6,540,776 B2 | 4/2003 | Sanders et al. | 623/1.15 |
| 6,568,235 B1 * | 5/2003 | Kokish | 72/402 |
| 6,576,005 B1 * | 6/2003 | Geitz | 623/1.11 |
| 6,576,006 B2 | 6/2003 | Limon et al. | 623/1.11 |
| 6,629,350 B2 * | 10/2003 | Motsenbocker | 29/283.5 |
| 6,629,992 B2 | 10/2003 | Bigus et al. | 623/1.12 |
| 6,640,412 B2 * | 11/2003 | Iancea | 29/505 |
| 6,651,478 B1 * | 11/2003 | Kokish | 72/402 |
| 6,666,880 B1 * | 12/2003 | Chiu et al. | 623/1.11 |
| 6,702,845 B1 * | 3/2004 | Cully et al. | 623/1.15 |
| 6,769,161 B2 * | 8/2004 | Brown et al. | 29/234 |
| 6,800,089 B1 * | 10/2004 | Wang | 623/1.44 |
| 6,808,533 B1 * | 10/2004 | Goodwin et al. | 623/1.13 |
| 6,823,576 B2 * | 11/2004 | Austin | 29/516 |
| 6,840,081 B2 * | 1/2005 | Kokish | 72/402 |
| 6,865,810 B2 * | 3/2005 | Stinson | 29/896.6 |
| 6,915,560 B2 * | 7/2005 | Austin | 29/722 |
| 6,925,847 B2 * | 8/2005 | Motsenbocker | 72/402 |
| 6,968,607 B2 * | 11/2005 | Motsenbocker | 29/505 |
| 6,988,881 B2 * | 1/2006 | Motsenbocker et al. | 425/392 |
| 7,096,554 B2 * | 8/2006 | Austin et al. | 29/282 |
| 7,152,452 B2 * | 12/2006 | Kokish | 72/402 |
| 7,207,204 B2 * | 4/2007 | Weber et al. | 72/402 |
| 7,225,518 B2 * | 6/2007 | Eidenschink et al. | 29/283.5 |
| 7,308,748 B2 * | 12/2007 | Kokish | 29/516 |
| 7,487,579 B2 * | 2/2009 | Eidenschink et al. | 29/515 |
| 7,636,997 B2 * | 12/2009 | Perreault et al. | 29/508 |
| 7,636,998 B2 * | 12/2009 | Tenhuisen et al. | 29/516 |
| 2001/0001890 A1 * | 5/2001 | Austin | 29/282 |
| 2002/0099431 A1 | 7/2002 | Armstrong et al. | 623/1.11 |
| 2002/0138129 A1 * | 9/2002 | Armstrong et al. | 623/1.11 |
| 2002/0138966 A1 * | 10/2002 | Motsenbocker | 29/516 |
| 2002/0161394 A1 * | 10/2002 | Macoviak et al. | 606/200 |
| 2002/0163104 A1 * | 11/2002 | Motsenbocker et al. | 264/320 |
| 2002/0198588 A1 * | 12/2002 | Armstrong et al. | 623/1.13 |
| 2003/0028237 A1 | 2/2003 | Sullivan et al. | 623/1.11 |
| 2003/0056360 A1 * | 3/2003 | Brown et al. | 29/516 |
| 2003/0070469 A1 * | 4/2003 | Kokish | 72/402 |
| 2003/0074049 A1 * | 4/2003 | Hoganson et al. | 623/1.13 |
| 2003/0099792 A1 * | 5/2003 | Andersson et al. | 428/35.2 |
| 2003/0113499 A1 * | 6/2003 | Sieber et al. | 428/40.1 |
| 2003/0192164 A1 * | 10/2003 | Austin | 29/505 |
| 2004/0123437 A1 * | 7/2004 | Kokish | 29/235 |
| 2004/0128818 A1 * | 7/2004 | Motsenbocker | 29/505 |
| 2004/0148007 A1 | 7/2004 | Jackson et al. | 623/1.12 |
| 2004/0167603 A1 * | 8/2004 | Jackson et al. | 623/1.12 |
| 2004/0181236 A1 * | 9/2004 | Eidenschink et al. | 606/108 |
| 2004/0199239 A1 * | 10/2004 | Austin et al. | 623/1.11 |
| 2004/0260379 A1 * | 12/2004 | Jagger et al. | 623/1.11 |
| 2005/0183259 A1 * | 8/2005 | Eidenschink et al. | 29/508 |
| 2008/0028594 A1 * | 2/2008 | Lafont et al. | 29/516 |
| 2009/0113693 A1 * | 5/2009 | Melsheimer | 29/516 |

* cited by examiner

METHOD TO SIMULTANEOUSLY LOAD AND COVER SELF EXPANDING STENTS

BACKGROUND OF THE INVENTION

Self expanding stents are used in coronary and peripheral vascular as well as endovascular applications. Specific vessels in which stents may be implanted include coronary arteries, renal arteries, peripheral arteries including iliac arteries, arteries of the neck and cerebral arteries, veins, biliary ducts, urethras, fallopian tubes, bronchial tubes, the trachea, the esophagus and the prostate.

Stents are available in a wide range of designs. Typically, stents are either mechanically expandable or self-expanding. Mechanically expandable stents are usually expanded with a balloon. An example of a mechanically expandable stent is a stent made from stainless steel. Self-expanding stents expand either as a result of a transformation of the material or because of the energy which has been stored therein. Examples of the former include stents made from shape memory materials including shape memory metals such as Nitinol and shape memory polymers. Examples of shape memory stents include Nitinol stents. Hybrid stents exhibiting properties of both self-expandable and mechanically expandable shaft are also known.

In use, stents are typically disposed about a delivery device and delivered to a desired location in a bodily vessel where they are then either allowed to self-expand or where they are mechanically expanded. Mechanically expanded stents are usually delivered on a balloon catheter. A stent is disposed about a balloon and at the desired time, the balloon is inflated with an inflation fluid. The expansion of the balloon, in turn, applies an outward force to the stent to expand the stent.

Self-expanding stents are typically plunged into a sheath in the form of a polymer tube on the delivery device. This maintains the stent in a reduced diameter configuration. At a desired time, the sheath is withdrawn, allowing the stent to self-expand. This reduced diameter enables the stent to be tracked to and access a given treatment site where the sheath is then retracted off the stent, allowing the stent to expand and oppose the vessel wall.

As the state of the art develops, self expanding stents in particular and self-expanding medical devices in general are trending toward larger and longer sizes. Also there is an increased effort toward development of drug eluting self expanding stents and other self-expanding medical devices.

With the trend toward longer and larger stents as well as drug coated stents and devices; there are complications with the current stent loading methods. For example, alignment becomes an issue with large diameter stents when trying to compress and load them in small sheaths. Also, frictional forces developed during loading increase with longer stents and may result in buckling of the stent or the sheath. The loading of a drug coated stent into a sheath can cause damage to the coating—especially on the longer and larger stent sizes. The various drug coatings can range from being brittle and poorly adhered to the stent material to being soft and of high tack relative to the stent material. Stent material may be, for example, Nitinol or stainless steel.

There remains a need for innovative methods for loading self-expanding stents and other self-expanding devices onto delivery catheters. There also remains a need for innovative devices which are capable of loading self-expanding stents and other self-expanding devices onto delivery catheters.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of at least a portion of the technical disclosure in the specification is provided as well for the purposes of complying with 37 C.F.R. 1.72.

All US patents and applications and all other published documents mentioned anywhere in this application are incorporated herein by reference in their entirety.

SUMMARY OF THE INVENTION

In one embodiment, the invention is directed to a method comprising the steps of providing a wrapped stent, compressing the wrapped stent and forming a sheath about the stent. The wrapped stent comprises a stent with a polymeric sheet disposed thereabout in one embodiment. The sheet has two opposing edges extending along at least a portion of the length of the stent. The sheath is formed about the stent by affixing at least one of the opposing edges of the polymeric sheet to a portion of the polymeric sheet adjacent thereto.

The method may further comprise the steps of providing a stent delivery device and securing the sheathed stent to the stent delivery device.

The step of providing a wrapped stent may include the steps of providing a stent, providing a polymeric sheet and disposing the polymeric sheet about the stent so that opposing edges of the sheet extend along the length of the stent.

The step of compressing may include the steps of disposing the wrapped stent in a compression device and pulling on at least one of the opposing edges of the sheet while applying or after applying a compressive force to the stent so as to tighten the polymeric sheet about the stent.

A seam may be visible on the wrapped stent following the affixing step. Desirably, however, a seam would not be visible or dimensionally discernable from the balance of the polymeric sheet.

The affixing step may be accomplished via a variety of different steps. An example of a suitable step includes adhesively affixing at least one of the edges of the polymeric sheet using a pressure sensitive adhesive, a one part adhesive, a two part adhesive or any other suitable type of adhesive. Other examples include affixing the edge to the polymeric sheet using a pressure sensitive tape, affixing the edge to the polymeric sheet via contact welding, affixing the edge to the polymeric sheet via solvent welding, via ultrasonic welding or via laser welding. In the case of welding, the compression device may comprise at least one heated blade which is used to contact weld the edge in place. The compression device may comprise at least one sacrificial blade which is fused to the polymeric sheet. The fusing may occur via the use of heat, solvent or any other suitable method. The sacrificial blade may be located on the tip of a loading blade, located where the joining occurs. Thus, for example, it may be located at the location of a seam. Desirably, the sacrificial material would be compatible with the sheath material and would be suitable for the process used to join the sheath into a tubular configuration. As such, the sacrificial material could be come a permanent part of the sheath.

Typically, in the practice of the invention, the stent will be self-expanding.

The invention is also directed to a method of securing a medical device to a medical device delivery apparatus. The method comprises the steps of providing a wrapped medical device, compressing the wrapped medical device and forming a sheathed medical device from the compressed medical device.

The wrapped medical device comprises a medical device with a polymeric sheet disposed thereabout but not affixed thereto. The sheet has two opposing edges extending along at least a portion of the length of the medical device. At least one of the opposing edges is affixed to a portion of the polymeric sheet adjacent thereto so as to form a sheathed medical device, the polymeric sheet forming a sheath about the medical device.

The compressing step may include the steps of disposing the wrapped medical device in a compression device and pulling on at least one of the opposing edges of the sheet while applying or after applying a compressive force to the medical device so as to tighten the polymeric sheet about the medical device.

Following the affixing step, a seam may be visible on the wrapped medical device. The presence of a seam desirably will not inhibit the performance of the medical device.

The securing step may include attaching the sheathed medical device to a sheath removal mechanism which is operatively associated with the medical device delivery apparatus such that the medical device, after the securing step, may be removed from the sheath upon activation of the sheath removal mechanism or such that the sheath may be removed from the medical device.

The method may further comprise the steps of providing a medical device delivery apparatus and securing the sheathed medical device to the medical device delivery apparatus.

Typically, the medical device will be a stent, a filter or an embolic protection device. The medical device may be in the form of an expandable framework, regardless of whether it is capable of stenting a vessel. In the case of a stent, the stent will desirably be self-expanding. Suitable filters include vena cava filters.

Additional details and/or embodiments of the invention are discussed below.

BRIEF DESCRIPTION OF THE FIGS.

FIG. 6b shows an enlarged portion of the stent delivery device of FIG. 6a.

DETAILED DESCRIPTION OF THE INVENTION

This invention may be embodied in many different forms. This description is an exemplification of the principles of the invention and is not intended to limit the invention to the particular embodiments illustrated.

For the purposes of this disclosure, unless otherwise indicated, identical reference numerals used in different figures refer to the same component.

Figure 1:
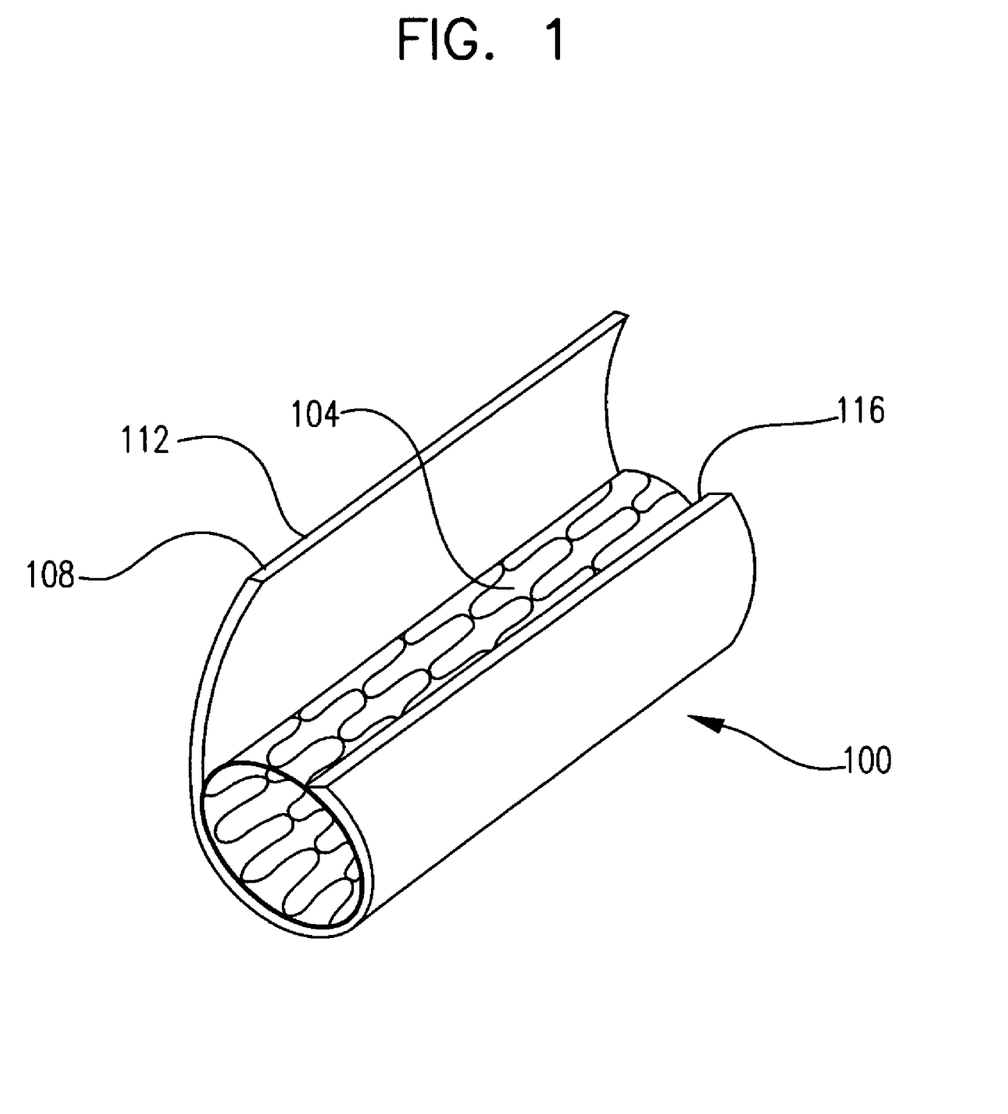
FIG. 1 shows a wrapped stent.

In one embodiment, the invention is directed to a method comprising the steps of providing a wrapped stent, compressing the wrapped stent and forming a sheath about the stent. The wrapped stent, as shown at 100 in FIG. 1, comprises stent 104 with polymeric sheet 108 disposed thereabout. Sheet 108 has two opposing edges 112 and 116 extending along at least a portion of the length of stent 104. Desirably, as shown in FIG. 1, the two opposing edges extend along the entire length of the stent.

Desirably, stent 104 will be a self-expanding stent. More desirably, stent 104 will be a coated self-expanding stent. The invention may also be practiced with balloon expandable stents, both bare and coated.

The sheath will desirably be made of any material strong enough to contain a compressed stent and flexible enough to be tracked on a delivery system in the body. Desirably, it will be such that it can be thermally attached to itself or tie layers. Suitable polymeric materials include known sheath materials such as those disclosed in U.S. Pat. No. 5,968,069 and U.S. Pat. No. 6,068,634. Examples of sheath materials include elastomers such as polyurethane, polyurethane blends, silicone, latex or polyether amide. Sheath materials may include thermoplastics including polyethylene, polypropylene, polyamide, polyimide, polyesters (polyethylene terephthalate) and polyethylene naphthalate.

Figure 2:
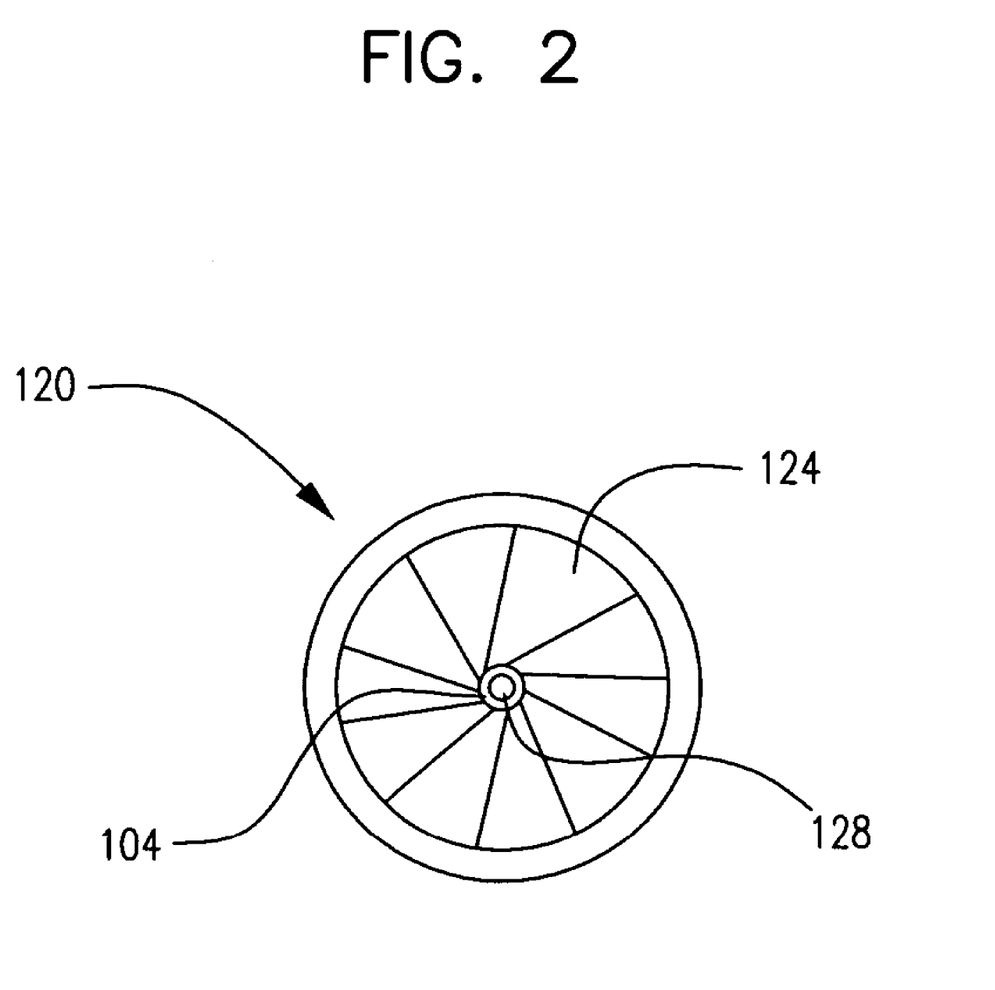
FIG. 2 shows a portion of a compression machine in cross-section.
Figure 3A:
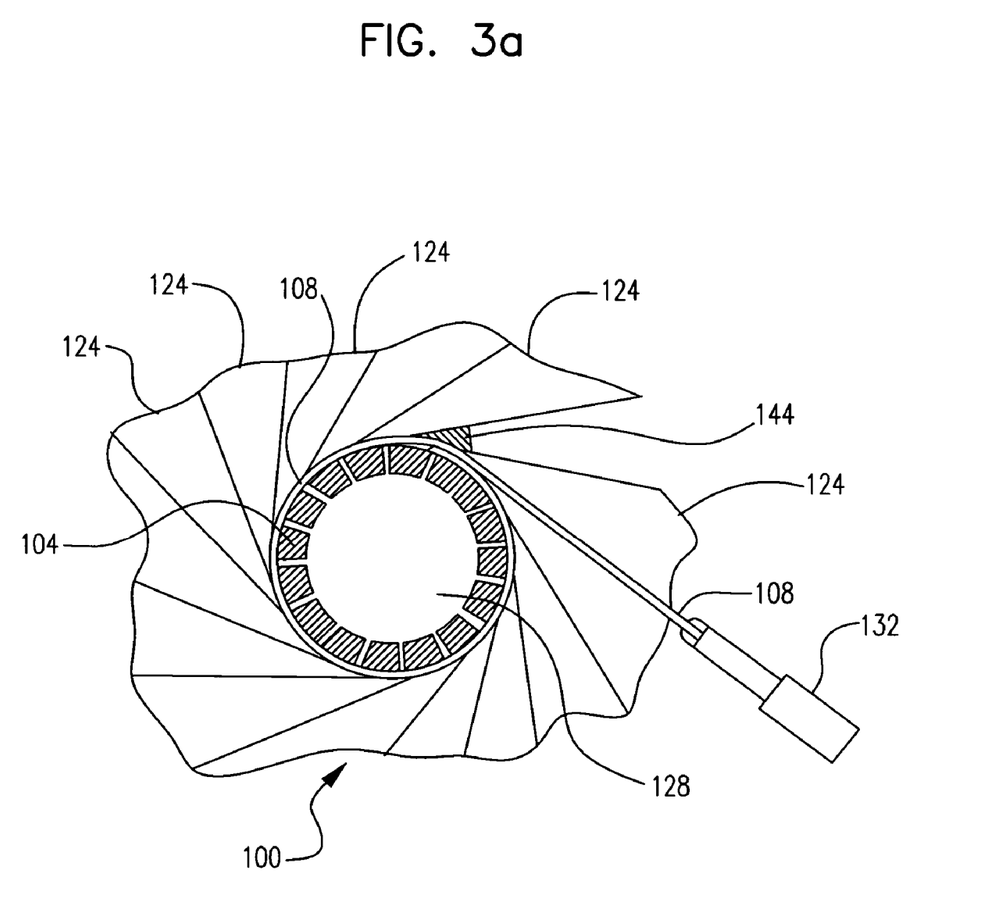
FIG. 3a shows tension applied to a polymeric sheet while the wrapped stent is being compressed.

Typically, as shown in FIG. 2, the stent will be compressed with a compression device such as an iris-type crimper shown generally in cross-section at 120. Compression device 120 includes a plurality of blades 124 disposed about an opening 128. The blades can be moved inward to apply an inward force to the stent so as to compress the stent. Other types of compression devices may also be used in the practice of the invention as discussed below. As shown in FIG. 3a, wrapped stent 100 is disposed in a compression device. At least one of the opposing edges of the sheet is pulled, as shown in FIG. 3a, and optionally both of the opposing edges of the sheet are pulled while applying or after applying a compressive force to the stent so as to tighten the polymeric sheet about the stent. Device 132 places the edge of the sheet under tension. By so doing, the polymeric sheet is wrapped more tightly around the stent and some slack is removed from the sheet. Desirably, the polymeric sheet will be wrapped as tightly as is needed to bring the stent down to and maintain a fully compressed state in which adjacent struts will typically be touching one another or nearly touching.

In the practice of the invention, any compression device may be used. Examples of such devices include that disclosed in U.S. Pat. No. 6,360,577 and that disclosed in US 20020138966. Typically, the device will be of the iris type, comprising a plurality of blades which are disposed about an opening and which can open and close in an iris-like manner. Other compression devices, however, may also be used in the practice of the invention.

Figure 4:
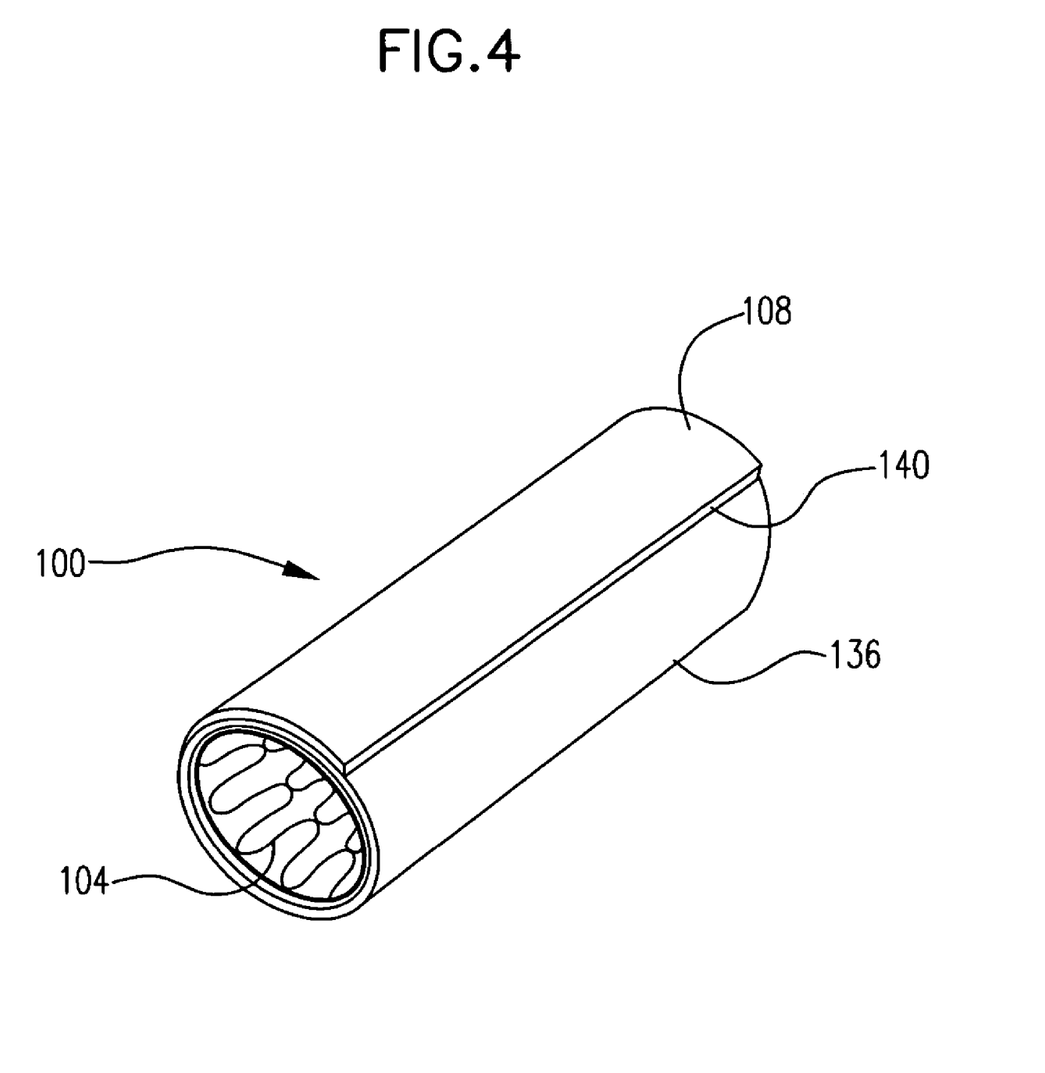
FIG. 4 shows formation of a sheath.

As shown in FIG. 4, sheath 136 is formed about stent 104 by affixing at least one of the opposing edges of the polymeric sheet to a portion of the polymeric sheet adjacent thereto. If necessary, excess polymeric material may be trimmed from the polymeric sheet prior to the affixing step, or from the sheath following the affixing step. A seam, shown at 140, may be visible on the wrapped stent following the affixing step. The sheath is disposed about the stent but is not affixed thereto and can be removed from the stent at later time by sliding the sheath off of the stent or by pulling the stent from the sheath.

In some embodiments, each opposing edge 112, 116 may be affixed to a portion of the polymeric sheet adjacent thereto.

In some embodiments, the polymeric sheet may be properly sized such that when the stent is in a fully compressed state, the opposing edges 112, 116 of the polymeric sheet may be affixed to one another or affixed while arranged in a slightly overlapping relationship.

An edge of the polymeric sheet may be attached to an adjacent portion of the polymeric sheet so to form the sheath in a variety of different ways.

An example of a suitable method includes adhesively affixing one of the edges to the polymeric sheet using a pressure sensitive adhesive, a one part adhesive, a two part adhesive or any other suitable type of adhesive. Suitable adhesives include, but are not limited to, liquid adhesives and pressure sensitive adhesives. Exemplary suitable adhesives materials for use include, but are not limited to one part adhesives—silicone room temperature vulcanization adhesives (RTVs), one part heat cured polyurethanes (air, heat and moisture cured), epoxies, acrylics, cyanoacrylics, methacrylics, epoxypolyurethanes (including anerobic one part adhesives, one part water-based adhesives), two-part adhesives—epoxies, urethane epoxies, urethane, polysulfides, urethane liquid moisture cure, pressure sensitive adhesives, polymerizable adhesives (including cyanoacrylates), resins (including aliphatic resins), polyurethane, polyvinyl acetate, contact cements, and hide glues, UV curable adhesives, hot melt adhesives, double-sided tape—containing acrylic and acrylic-epoxy adhesives.

Figure 3B:
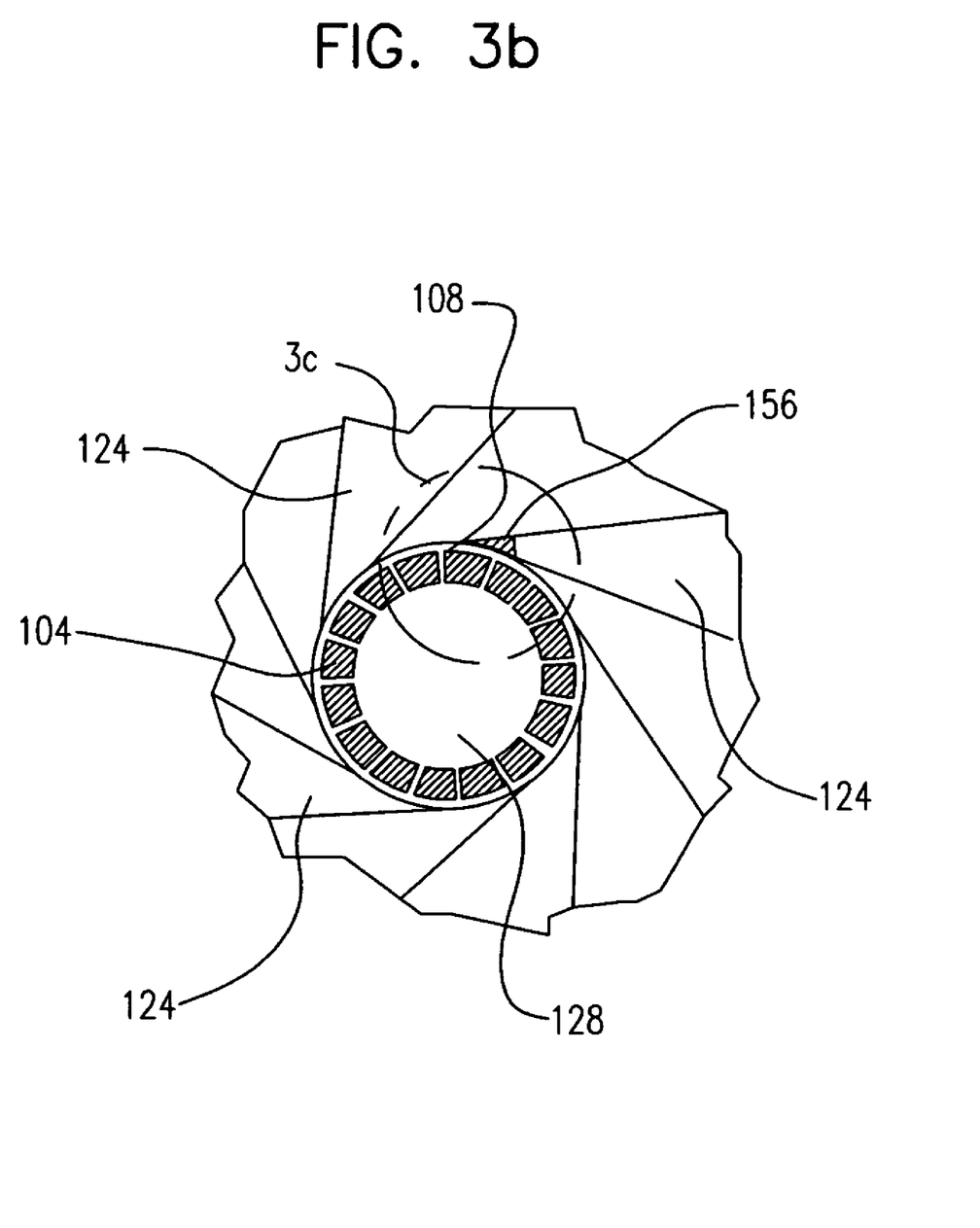
FIG. 3b shows a sheath and a stent in a crimper having a blade with a sacrificial tip.

Other examples of suitable methods include affixing the edge to the polymeric sheet using a pressure sensitive tape, affixing the edge to the polymeric sheet via contact welding, affixing the edge to the polymeric sheet via solvent welding or via ultrasonic welding. Examples of tapes are disclosed above. In the case of welding, the compression device, as shown in FIG. 3a, may comprise at least one heated blade 144 which is used to contact weld the edge in place. In one embodiment, as shown in FIG. 3b, the compression device may comprise at least one sacrificial blade. The sacrificial blade may be in the form of blade 124 which has at its tip a sacrificial material 156. The sacrificial blade may optionally be heated. The sacrificial material may be used to fill in any gap, as shown at 158 in FIG. 3c, in the sheath, for example, between the edges of the sheath. This may be accomplished by fusing the sacrificial material to the sheath. The sacrificial material will desirably be thermally compatible with the sheath and/or compatible with the sheath from a bonding perspective.

Figure 5:
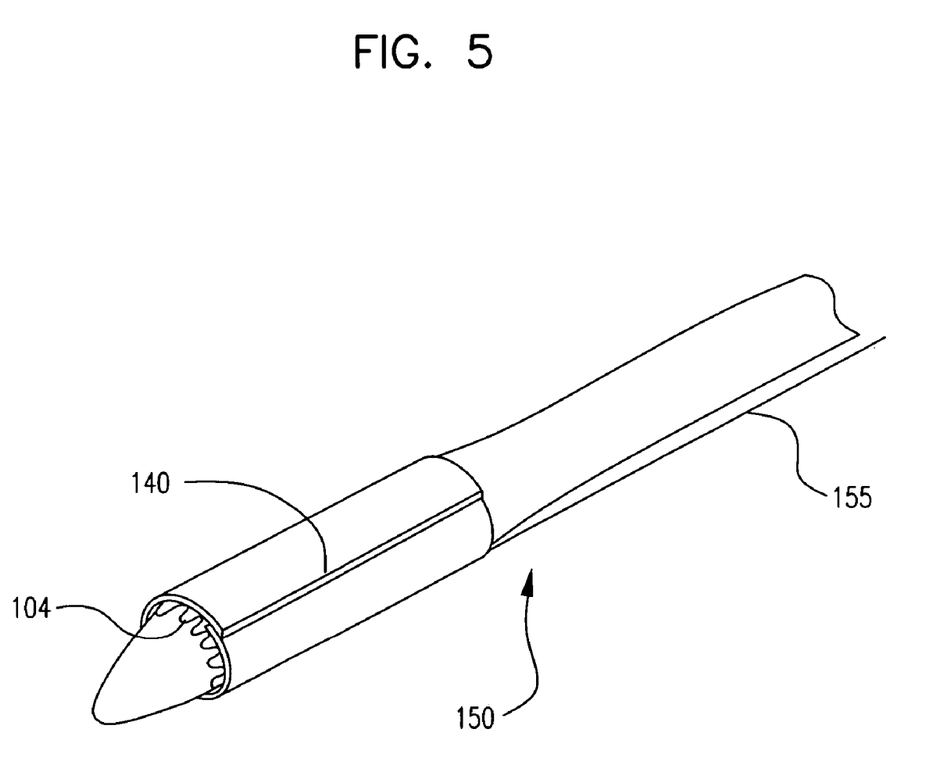
FIG. 5 shows a stent delivery device.
Figure 6A:
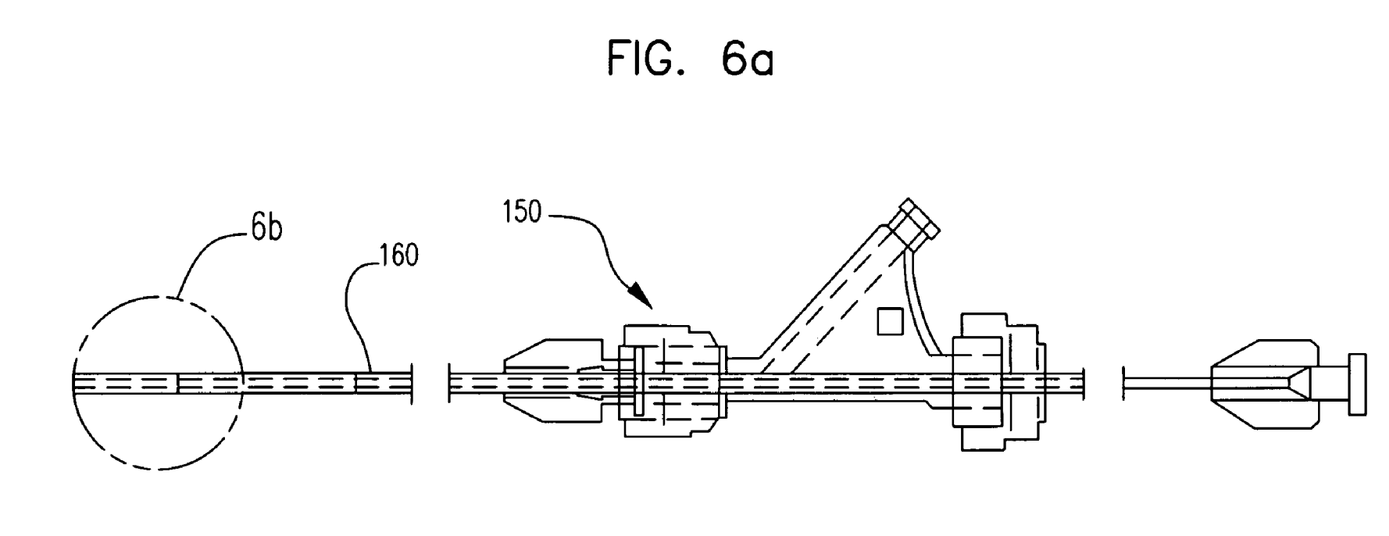
FIG. 6a shows a stent delivery device.
Figure 6B:
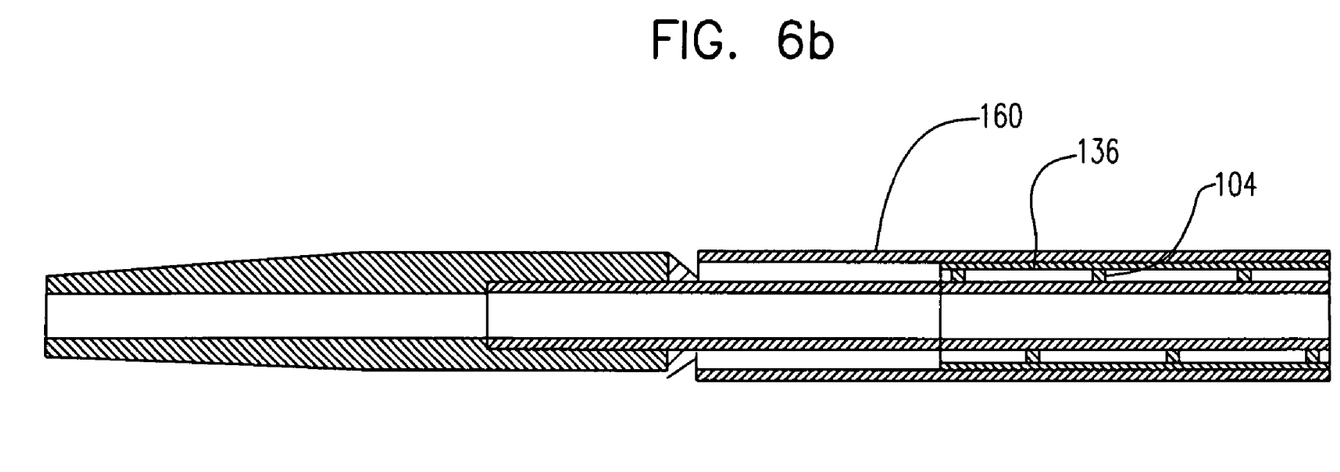

Following compression, a stent delivery device such as that shown generally at 150 in FIG. 5 or that shown generally at 150 in FIGS. 6a and 6b may be provided. FIG. 6b shows an enlarged view of detail A of the distal end of the stent delivery device of FIG. 6a. The sheath may be attached, using standard joining processes including, but not limited to adhesive bonding, RF bonding and laser bonding or via any other suitable technique, to a sheath withdrawal device. As shown in FIGS. 6a and 6b, the sheath withdrawal device is in the form of a movable tube 160. The sheath withdrawal device may be in the form of a pull wire or any other suitable device. The stent delivery device should be suitable for the type of stent to be delivered. In the case of self-expanding stents, or more generally, self-expanding medical devices, a catheter configured for delivering self-expanding stents or other medical devices will be used. Such a catheter will desirably have a device which can be attached to the sheath to remove the sheath from the stent at the appropriate time. This may be accomplished in a number of ways including by attaching a pull wire 155 to the sheath. Catheters are well known in the art and catheters such as those disclosed in U.S. Pat. No. 5,772,669 and U.S. Pat. No. 6,120,522 may be modified for use in the present invention.

The method may further comprise the steps of inserting the stent delivery catheter or more generally, the medical device delivery catheter in a bodily vessel, delivering the stent or medical device to a desired bodily location, withdrawing the sheath from the stent or medical device and expanding the stent or medical device. The sheath may then be withdrawn from the body.

In the case of a balloon expandable stent, or more generally a balloon expandable medical device, a typical balloon catheter may be used. The balloon catheter will have to be suitably modified, however, to allow for easy removal of the sheath from the stent or other medical device after it has been disposed about the balloon or other expandable member of the catheter. The use of the inventive methods disclosed herein in conjunction with balloon expandable stents may be of particular value in conjunction with drug coated stents. For such stents, it may be desirable to provide a sheath about a stent so that when the stent is crimped onto the balloon or other expandable member, the drug coating will not be damaged. To that end, the invention is also directed to any of the inventive methods disclosed herein in which drug coated stents, balloon expandable or mechanically expandable, are used.

The stents used in the practice of the inventive, or more generally, the implantable medical devices, may also be a hybrid device, being both balloon expandable in-part and self-expanding in-part.

In FIGS. 1, 4 and 5, the sheath will have seam which extends parallel to the longitudinal axis of the stent or medical device. It is also within the scope of the invention for the resulting seam to be non-parallel to the longitudinal axis of the stent or medical device. For example, the sheath may be wrapped spirally about the medical device so as to have a spiral seam. Other shaped seams are also within the scope of the invention. The seam need not be continuous and may be interrupted.

The invention is also directed to a method of securing a medical device to a medical device delivery apparatus. The method comprises the steps of providing a wrapped medical device, compressing the wrapped medical device and forming a sheathed medical device from the compressed medical device.

The wrapped medical device comprises a medical device with a polymeric sheet disposed thereabout. The sheet has two opposing edges extending along at least a portion of the length of the medical device. At least one of the opposing edges is affixed to a portion of the polymeric sheet adjacent thereto so as to form a sheathed medical device, the polymeric sheet forming a sheath about the medical device.

The compressing step may include the steps of disposing the wrapped medical device in a compression device and pulling on at least one of the opposing edges of the sheet while applying or after applying a compressive force to the medical device so as to tighten the polymeric sheet about the medical device.

Following the affixing step, desirably, a seam is visible on the wrapped medical device.

The securing step may include attaching the sheathed medical device to a sheath removal mechanism which is operatively associated with the medical device delivery apparatus such that the medical device, after the securing step, may be removed from the sheath upon activation of the sheath removal mechanism.

The method may further comprise the steps of providing a medical device delivery apparatus and securing the sheathed medical device to the medical device delivery apparatus.

Typically, the medical device will be a stent, a filter or an embolic protection device. In the case of a stent, the stent will desirably be self-expanding. Suitable filters include vena cava filters.

The invention is also directed to a medical device delivery catheter, such as that shown at 150 in FIG. 5. Medical device delivery catheter 150 includes a catheter tube 190 with a sheathed medical device 100 disposed thereabout. Sheathed medical device 100 includes a medical device such as a stent, desirably self-expanding, a filter or an embolic protection device, and a sheath disposed thereabout, the sheath having a seam.

Figure 3C:
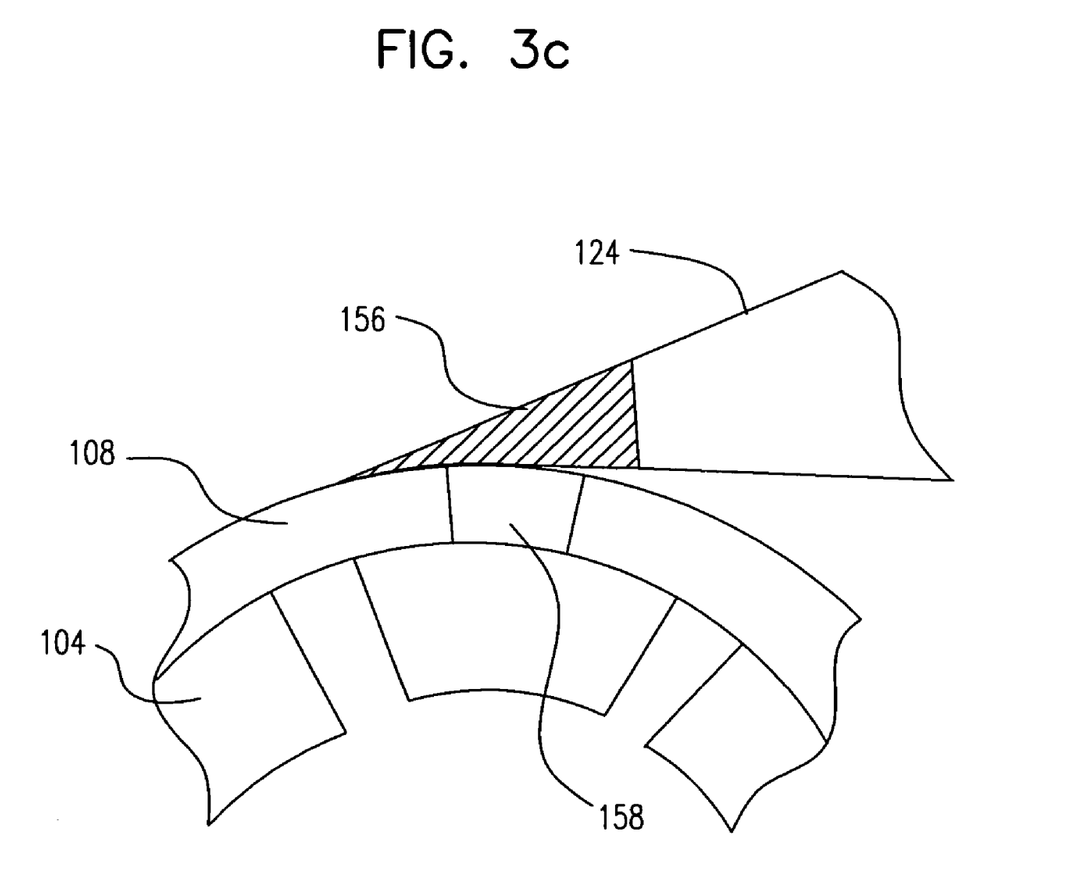
FIG. 3c shows an enlargement of region 3c of FIG. 3b.

The invention is further directed to a compression device comprising at least one sacrificial blade which may be fused to the polymeric sheet. An example of such a device is shown in FIG. 3c, wherein a blade 124 is shown having a sacrificial tip 156. The sacrificial blade may be located on the tip of a loading blade, located where the joining occurs. Thus, for example, it may be located at the location of a seam. Desirably, the sacrificial material would be compatible with the sheath material and would be suitable for the process used to join the sheath into a tubular configuration.

The invention is also directed to a medical device which is provided with a sheath using any of the inventive methods disclosed herein. In one embodiment, the invention is directed to a sheathed medical device wherein the sheath has a seam. The seam may be parallel to longitudinal axis of the medical device, may spiral about the longitudinal axis or may assume some other configuration. The medical device may be any of those disclosed herein including, but not limited to stents.

The invention is also directed to a medical delivery device comprising any of the sheathed medical devices disclosed herein and a catheter.

The stents and other medical devices to be sheathed in the practice of the invention may be of any suitable design and material including polymeric materials, metals, ceramics and composites. Suitable polymeric materials include but are not limited to thermo tropic liquid crystal polymers (Lip's). Suitable metals include but are not limited to stainless steel, cobalt chrome alloys such as edgily, tantalum or other plastically deformable metals. Other suitable metals include but are not limited to shape-memory metals such as nickel titanium alloys generically known as "nitinol", platinum/tungsten alloys and titanium alloys.

The stents and other medical devices may include suitable radiopaque coatings. For example, they may be coated with gold or other noble metals or sputtered with tantalum or other metals. They may also be made directly from a radiopaque material to obviate the need for a radiopaque coating or may be made of a material having a radiopaque inner core. Other radiopaque metals which may be used include platinum, platinum tungsten, palladium, platinum iridium, rhodium, tantalum, or alloys or composites of these metals.

As discussed above, the stents and other medical devices to be sheathed may also be provided with various bio-compatible coatings to enhance various properties of the device. For example, they may be provided with lubricious coatings. They may also be provided with drug-containing coatings which release drugs over time.

To that end, the use of other coatings on the inventive stents and other medical devices is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anticoagulants such as D-Phe-Pro-Arg chloromethyl keton, an RGD peptide-containing compound, heparin, antithrombin compounds, platelet receptor antagonists, antithrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha. and .beta., platelet-derived endothelial growth factor, platelet-derived growth factor, tumor necrosis factor alpha., hepatocyte growth factor and insulin like growth factor, cell cycle inhibitors including CD inhibitors, thymidine kinase ("TK") and other agents useful for interfering with cell proliferation the family of bone morphogenic proteins ("BMP's"),BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL™), fibrin, collagen and derivatives thereof, polysaccharides such as celluloses, starches, dextrans, alginates and derivatives, hyaluronic acid, squalene emulsions. Polyacrylic acid, available as HYDROPLUS™ (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The stents and other medical devices to be sheathed may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers. The medical devices to be sheathed may include expandable frameworks, regardless of whether they are capable of maintaining the patency of a vessel.

The stents and other medical devices to be sheathed may find use in coronary arteries, renal arteries, peripheral arteries including iliac arteries, arteries of the neck and cerebral arteries. They are not, however, limited to use in the vascular system and may also be advantageously employed in other body structures, including but not limited to arteries, veins, biliary ducts, urethras, fallopian tubes, bronchial tubes, the trachea, the esophagus and the prostate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The above disclosure is intended to be illustrative and not exhaustive. These examples and this description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A method comprising the steps of:
   providing a wrapped stent, the wrapped stent comprising a stent with a polymeric sheet disposed thereabout, the sheet having two opposing edges extending along at least a portion of the length of the stent;
   compressing the wrapped stent in a compression device to form a wrapped compressed stent;
   subsequent to at least a portion of the compressing of the wrapped stent, affixing at least one of the opposing edges to a portion of the polymeric sheet adjacent thereto so as to form a sheathed compressed stent, the polymeric sheet forming a sheath disposed about but not affixed to the stent, the sheath retaining the stent in the compressed state.

2. The method of claim 1 further comprising the steps of:
   providing a stent delivery device;
   securing the sheathed stent to the stent delivery device.

3. The method of claim 2 wherein the stent is self-expanding.

4. The method of claim 2 wherein the step of providing a wrapped stent comprises the steps of:
   providing a stent;
   providing a polymeric sheet;
   disposing the polymeric sheet about the stent so that two opposing edges of the sheet extend along the length of the stent.

5. The method of claim 1, wherein the compressing step comprises compressing the wrapped stent while simultaneously applying tension to the polymeric sheet in a direction lateral to said stent.

6. The method of claim 1, further comprising trimming excess polymeric material from the sheathed compressed stent.

7. A method comprising the steps of:
   providing a wrapped stent, the wrapped stent comprising a stent with a polymeric sheet disposed thereabout, the sheet having two opposing edges extending along at least a portion of the length of the stent;
   compressing the wrapped stent;
   subsequent to at least a portion of the compressing of the wrapped stent, affixing at least one of the opposing edges to a portion of the polymeric sheet adjacent thereto so as to form a sheathed compressed stent, the polymeric sheet forming a sheath disposed about but not affixed to the stent;
   providing a stent delivery device; and
   securing the sheathed stent to the stent delivery device;
   wherein the step of providing a wrapped stent comprises the steps of:
   providing a stent;
   providing a polymeric sheet; and
   disposing the polymeric sheet about the stent so that two opposing edges of the sheet extend along the length of the stent; and
   wherein the compressing step includes the steps of:
   disposing the wrapped stent in a compression device; and
   pulling on at least one of the opposing edges of the sheet in a stent lateral direction while applying or after applying a compressive force to the stent so as to tighten the polymeric sheet about the stent.

8. The method of claim 7 wherein a seam is visible on the wrapped stent following the affixing step.

9. The method of claim 8 further comprising the step delivering the sheathed stent to a desired bodily location, withdrawing the sheath from the stent and implanting the stent in the body.

10. The method of claim 7 wherein during the affixing step one of the edges is adhesively affixed to the polymeric sheet.

11. The method of claim 7 wherein during the affixing step one of the edges is adhesively affixed to the polymeric sheet using a pressure sensitive adhesive.

12. The method of claim 7 wherein during the affixing step one of the edges is affixed to the polymeric sheet using a pressure sensitive tape.

13. The method of claim 7 wherein during the affixing step one of the edges is affixed to the polymeric sheet via contact welding.

14. The method of claim 7 wherein during the affixing step one of the edges is affixed to the polymeric sheet via solvent welding.

15. The method of claim 7 wherein during the affixing step one of the edges is affixed to the polymeric sheet via ultrasonic welding.

16. A method comprising the steps of:
   providing a stent;
   providing a polymeric sheet;

disposing the polymeric sheet about the stent so that two opposing edges of the sheet extend along at least a portion the length of the stent to form a wrapped stent, the wrapped stent comprising a stent with a polymeric sheet disposed thereabout;

compressing the wrapped stent by disposing the wrapped stent in a compression device and pulling on at least one of the opposing edges of the sheet while applying or after applying a compressive force to the stent so as to tighten the polymeric sheet about the stent;

affixing at least one of the opposing edges to a portion of the polymeric sheet adjacent thereto via contact welding so as to form a sheathed stent, the polymeric sheet forming a sheath disposed about but not affixed to the stent;

providing a stent delivery device; and securing the sheathed stent to the stent delivery device;

wherein the compression device comprises at least one heated blade which is used to contact weld the edge in place.

17. A method comprising the steps of:

providing a stent;

providing a polymeric sheet;

disposing the polymeric sheet about the stent so that two opposing edges of the sheet extend along at least a portion of the length of the stent to form a wrapped stent, the wrapped stent comprising a stent with a polymeric sheet disposed thereabout;

compressing the wrapped stent by disposing the wrapped stent in a compression device and pulling on at least one of the opposing edges of the sheet while applying or after applying a compressive force to the stent so as to tighten the polymeric sheet about the stent;

affixing at least one of the opposing edges to a portion of the polymeric sheet adjacent thereto so as to form a sheathed stent, the polymeric sheet forming a sheath disposed about but not affixed to the stent providing a stent delivery device; and securing the sheathed stent to the stent delivery device;

wherein the compression device comprises at least one sacrificial blade which is fused to the polymeric sheet.

18. A method of securing a medical device to a medical device delivery apparatus comprising the steps of:

providing a wrapped medical device, the wrapped medical device comprising a medical device with a polymeric sheet disposed thereabout, the sheet having two opposing edges extending along at least a portion of the length of the medical device;

reducing the size of the wrapped medical device;

subsequent to at least a portion of the reducing of the size of the wrapped medical device, affixing at least one of the opposing edges to a portion of the polymeric sheet adjacent thereto so as to form a sheathed medical device, the polymeric sheet forming a sheath disposed about but not affixed to the medical device, the sheath retaining the stent in the compressed state;

providing a medical device delivery apparatus;

securing the sheathed medical device to the medical device delivery apparatus.

19. The method of claim 18 wherein the medical device is a self-expanding stent.

20. The method of claim 18 wherein the medical device is a self-expanding filter.

21. The method of claim 18 wherein the reducing step includes the steps of:

disposing the wrapped medical device in a compression device;

pulling on at least one of the opposing edges of the sheet in direction lateral to said medical device while applying or after applying a compressive force to the medical device so as to tighten the polymeric sheet about the medical device.

22. The method of claim 21 wherein a seam is visible on the wrapped medical device following the affixing step.

23. The method of claim 21 wherein the securing step comprises attaching the sheathed medical device to a sheath removal mechanism operatively associated with the medical device delivery apparatus such that the medical device, after the securing step, may be removed from the medical device delivery apparatus upon activation of the sheath removal mechanism.

24. A method comprising the steps of:

providing a wrapped stent, the wrapped stent comprising a stent with a polymeric sheet disposed thereabout, the sheet having two opposing edges extending along at least a portion of the length of the stent;

compressing the wrapped stent; and subsequent to at least a portion of the compressing of the wrapped stent, affixing at least one of the opposing edges to a portion of the polymeric sheet adjacent thereto so as to form a sheathed stent, the polymeric sheet forming a sheath disposed about but not affixed to the stent;

wherein the compressing step comprises disposing the wrapped stent in a compression device such that a portion of the polymeric sheet extends between two immediately adjacent blades of the compression device.

\* \* \* \* \*